United States Patent [19]

Swoyer et al.

[11] Patent Number: 6,026,567
[45] Date of Patent: *Feb. 22, 2000

[54] MEDICAL LEAD WITH STRANDED CONDUCTORS

[75] Inventors: John M. Swoyer, Andover; Diane M Radloff, Ramsey; Peter B. Mc Intyre, Mounds View; Timothy G. Laske, Shoreview, all of Minn.

[73] Assignee: Medtronic, Inc., Minneapolis, Minn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/439,332

[22] Filed: May 11, 1995

[51] Int. Cl.⁷ .................................................. H01K 3/10
[52] U.S. Cl. .............................. 29/854; 29/825; 29/872; 29/863; 607/122; 607/126
[58] Field of Search .............................. 29/854, 863, 871, 29/872, 825; 607/122, 126; 128/642

[56] References Cited

U.S. PATENT DOCUMENTS

| | | |
|---|---|---|
| 3,902,501 | 9/1975 | Citron . |
| 4,387,727 | 6/1983 | Sandstrom ................................ 607/122 |
| 4,432,377 | 2/1984 | Dickhudt ................................ 29/863 X |
| 4,538,623 | 9/1985 | Proctor et al. ........................... 607/122 |
| 4,559,951 | 12/1985 | Dahl et al. ................................ 128/642 |
| 4,572,605 | 2/1986 | Hess . |
| 4,922,607 | 5/1990 | Doan et al. ........................... 29/872 X |
| 4,964,414 | 10/1990 | Handa . |
| 5,014,720 | 5/1991 | Barcel et al. ........................... 607/122 |
| 5,246,014 | 9/1993 | Williams . |
| 5,324,321 | 6/1994 | Pohndorf . |

*Primary Examiner*—Lee Young
*Assistant Examiner*—Rick Kiltae Chang
*Attorney, Agent, or Firm*—Reed A. Duthler; Harold R. Patton

[57] ABSTRACT

A method of interconnecting a core, a stranded conductor such as a wire rope or cable and a component of a medical electrical lead provided with a internal lumen. At least one of the core and the internal lumen of the component is provided with a textured surface, such as threading. The conductor is located alongside said textured surface and the core is advanced into the lumen of said component, such that the textured surface engages the conductor and retains the conductor as the core is advanced into the lumen, and the conductor is compressed between the core and the inner lumen of the component.

9 Claims, 5 Drawing Sheets

MEDICAL LEAD WITH STRANDED CONDUCTORS

BACKGROUND OF THE INVENTION

The present invention relates to implantable medical electrical leads, and more particularly relates to multi-lumen, multi-conductor leads.

In the context of implantable electrical leads, such as those employed in conjunction with implantable pacemakers, implantable nerve stimulators, and implantable cardioverter/defibrillators, conductors typically have been either tinsel wire or coiled conductors. Recently, however, there has been an increasing level of interest in the use of new conductor types. One of the most promising new conductor types is the wire rope or cable (hereafter cable) conductor, comprising multiple strands, each strand comprising a number of very fine wires. In some cases, the conductors are provided with a thin coating of teflon or other insulating polymer. Examples of such conductors are described in U.S. Pat. No. 5,324,321 issued to Pohndorf et al., in U.S. Pat. No. 5,246,014, issued to Williams et al. and U.S. Pat. No. 4,964,414, issued to Handa et al., all incorporated herein by reference in their entireties.

In working cable type conductors, the inventors have determined that there are some difficulties associated with coupling the conductors to connectors, electrodes, sensors or other components. In particular, such conductors, in the sizes used for implantable electrical leads, are difficult to crimp, and the very fine wires employed tend to melt when welded. Moreover, if insulated, the cables typically must be stripped at their ends, prior to attachment.

SUMMARY OF THE INVENTION

The present invention addresses the problems of coupling cable type conductors to electrodes, connectors, sensors and other components in the context of implantable medical leads. Typically, the invention will take the form of a lead having a body formed of an elongated insulative tube with a lumen containing a conductor, typically coupled at its distal end to an electrode or a sensor and coupled at its proximal end to an electrical connector. The component to which the conductor is connected is provided with an internal lumen into which an end of the conductor and a core are inserted. Either the core or the inner lumen of the component is provided with threading or similar surface texture which engages the conductor. If the threading is on the core, the conductor is placed alongside the core and the core is advanced into the component's lumen, pulling the cable into component's lumen as the core is advanced. Conversely, if the threading is provided on the interior surface of the component's lumen, the cable is placed in the lumen, and the core is advanced into the lumen, with the cable retained in place by the threading. The core is sized so that the conductor is compressed between the core and the component's lumen to provide for electrical and mechanical coupling of the conductor to the component. If the conductor is insulated, the insulation simply shears off as the core is advanced, flowing into the spaces between adjacent threads, eliminating the necessity of stripping the end of the conductor prior to connection.

DETAILED DESCRIPTION OF THE PREFERRED EMBODIMENTS

Figure 1:
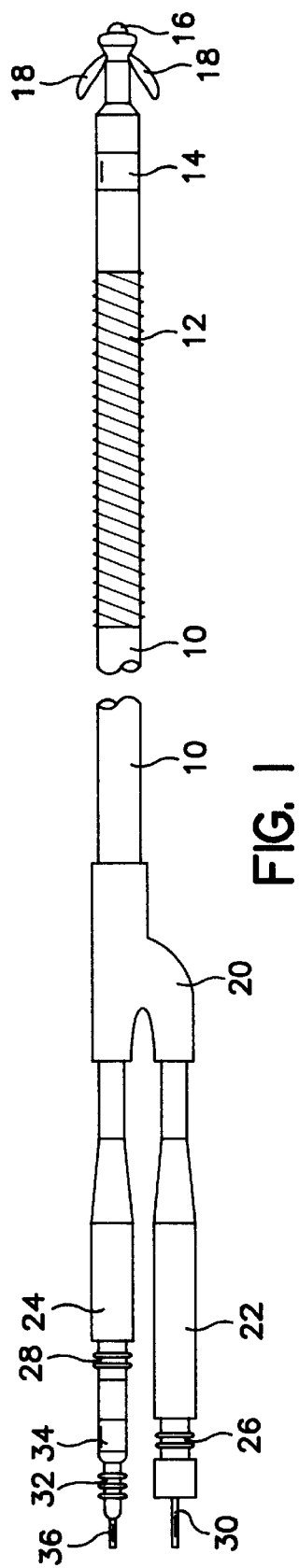
FIG. 1 is a plan view of an implantable lead of the type in which the present invention may be practiced.

FIG. 1 is a plan view of a defibrillation lead of the type in which the present invention may usefully be practiced. The present invention, of course, may also be usefully practiced in the context of other medical electrical leads, such as cardiac pacing leads, nerve and muscle stimulation leads, and so forth.

The lead of FIG. 1 is provided with an elongated insulative lead body 10, preferably fabricated of silicone rubber, polyurethane or other biocompatible elastomer. At the proximal end of the lead, it carries an elongated defibrillation electrode 12, a ring electrode 14 and a tip electrode 16, each coupled to a conductor located within the lead body 10. Tines 18 are employed to maintain electrode 16 in contact with the tissue of the right ventricle, as described in U.S. Pat. No. 3,902,501, issued to Citron. Electrodes 16, 14 and 12 may correspond to conventional, currently available pacing and defibrillation electrodes. The proximal end of the lead carries a connector assembly, beginning with a molded lead bifurcation 20, which splits off two of the conductors within lead body 10 to a bipolar, in-line connector assembly 24, generally corresponding to the IS-1 connector standard for pacing leads. Connector assembly 24 is provided with a first set of sealing rings 28, a connector ring 34, a second sealing rings 32 and connector pin 36. Connector pin 36 is coupled to a conductor which extends through the lead body 10 to tip electrode 16. Connector ring 34 is coupled to a conductor which extends through the lead body 10 to ring electrode 14. Connector assembly 22 carries a set of sealing rings 26 and a connector pin 30, coupled to a conductor extending through lead body 10 to defibrillation electrode 12. The illustrated connector assemblies are conventional elements, and may correspond to any of the numerous known electrical connector assemblies provided on implantable medical leads.

Although not visible in FIG. 1, it should be noted that the elongated conductors passing through lead body 10 may include any of the various known available conductors for use in conjunction with implantable electrical leads, including monofilar or multifilar coiled conductors, cable type conductors, and the like. In the specific context of the lead illustrated in FIG. 1, the conductor coupling connector pin 36 to electrode 16 takes the form of a multifilar coiled conductor to allow passage of a stylet therethrough, while the conductors coupling ring electrode 14 to connector ring 34 and coupling defibrillation electrode 12 to connector pin 30 take the form of cables provided with a coating of PTFE. In the embodiments discussed herein, the cables may be fabricated from silver cored MP35N wire, the cables including seven strands, each strand including seven wires, the cable being coated with an extruded coating of PTFE, and having an overall diameter of 0.017 inches (0.432 millimeters). However, the present invention is believed workable in the context of any stranded conductors appropriate for use in implantable electrical leads.

Figure 2:
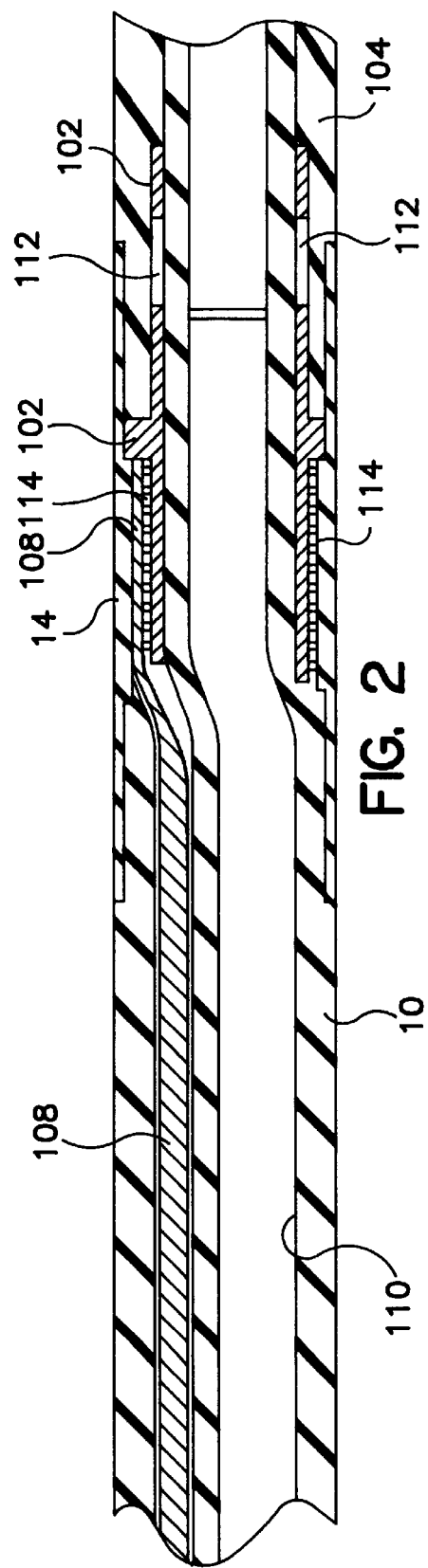
FIG. 2 is a sectional view through the body of the lead of FIG. 1 in the vicinity of the ring electrode.

FIG. 2 is a sectional view through the lead of FIG. 1 in the vicinity of ring electrode 14. In this view it can be seen that the lead body 10 is provided with at least two lumens, one of which carries cable 108. In FIG. 2, lumen 110 is illustrated as empty. However, in an actual lead as illustrated in FIG. 1, lumen 110 would contain a conductor coupling tip electrode 16 to connector pin 36. As described above, this would typically be an insulated, coiled conductor defining a central lumen allowing passage of a stylet therethrough. Cross bore 112 through core 102 allows for backfill of adhesive to bond the lead body 10 to a distal insulative sleeve 104, thereby also providing a mechanical interlock with the assembly of core 102 and ring electrode 14.

Conductor 108 is shown compressed between electrode 14 and threaded core 102, in order to maintain electrical and mechanical contact between conductor 108 and ring electrode 14. The distal end of threaded core 102, located within ring electrode 14, is provided with an outer surface having threads 115 machined therein. For example, threads having a pitch of 125 threads per inch, a depth of 0.002" and a flat of 0.002" on the crest of each thread may be employed. Core 102 may be fabricated of an implantable grade stainless steel or other implantable metal and electrode 14 may be fabricated of platinum/iridium alloy. In the illustrated embodiment, the threaded distal portion of core 102 has an outer diameter of 0.059", with the inner diameter of electrode 14, in its central portion, being 0.063". To assemble the ring electrode 14 to the conductor 108, the conductor 108 is first threaded through ring electrode 14 from its proximal end and placed along the threaded portion of threaded core 102. Threaded core 102 is then driven proximally into ring electrode 14, such that conductor 108 is compressed between the threaded portion of core 102 and the central portion of ring electrode 14 to provide a reliable mechanical and electrical interconnection.

Figure 3:
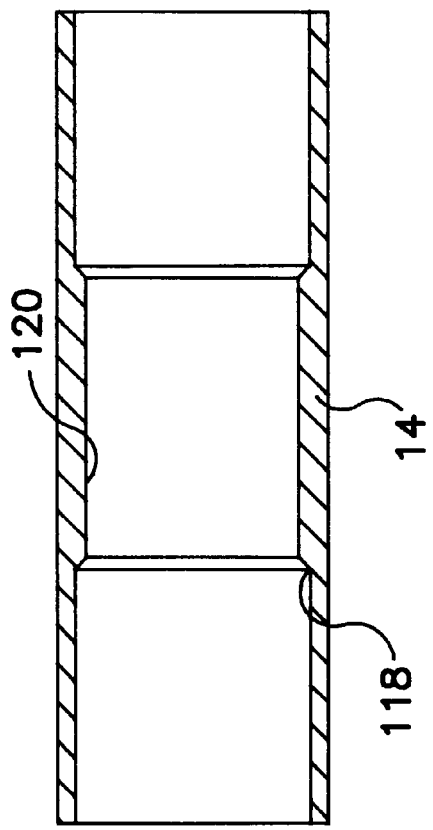
FIG. 3 is a sectional view of the ring electrode illustrated in FIG. 2.

FIG. 3 is a sectional view through ring electrode 14, removed from its surrounding components. In this view it can be seen that the ring electrode is provided with a reduced diameter central portion 120, and proximal and distal end portions having an increased diameter. Located at the proximal end of central portion 120 is a shoulder 118 which serves to limit the insertion depth of core 102.

Figure 4:
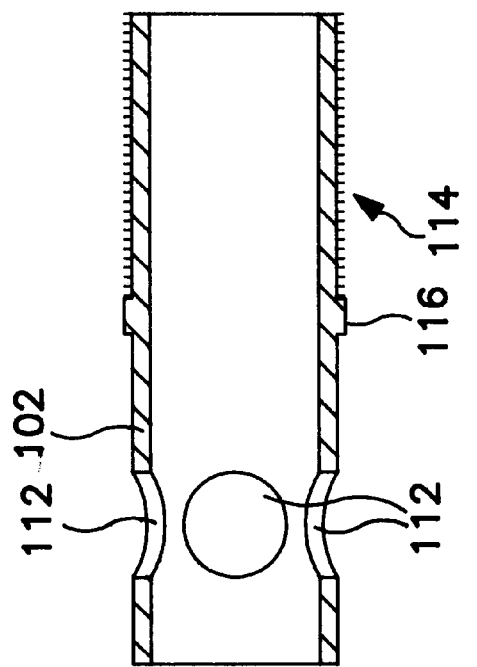
FIG. 4 is a sectional view of the threaded core illustrated in FIG. 2.

FIG. 4 illustrates core 102 in more detail. The distal portion 114 of core 102 is provided with threading 115, as described above, which extends to a point adjacent shoulder 116. Shoulder 116, in conjunction with shoulder 118, limits the insertion depth of core 102 into ring electrode 14. Also visible in this view are cross bores 112, which as described above, allow for backfilling of adhesive to couple the lead body 10 to the distal sheath 104 and core 102.

Figure 5:
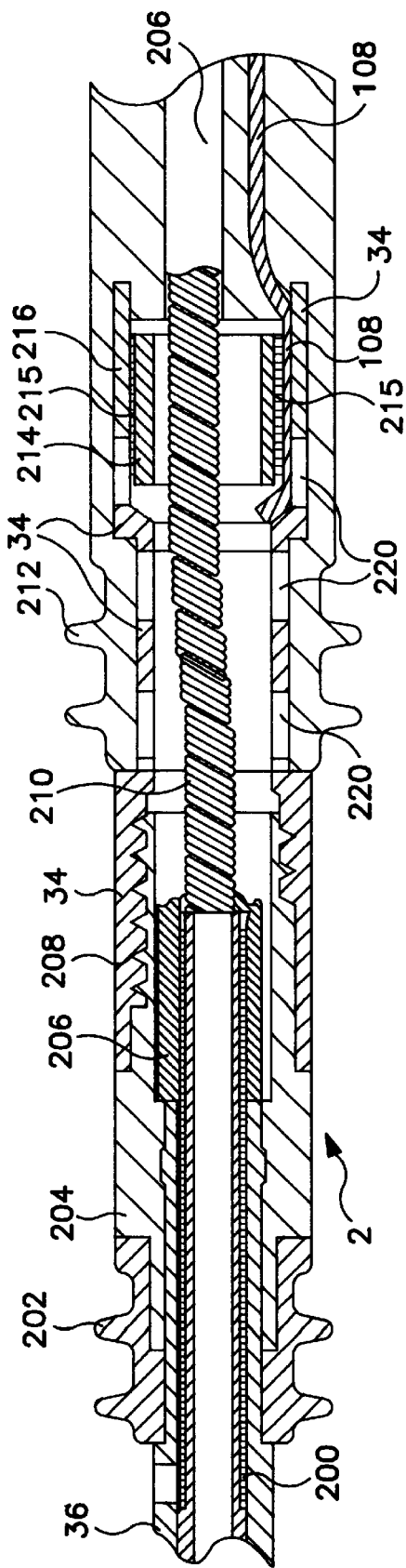
FIG. 5 is a sectional view through the body of the lead of FIG. 1 in the vicinity of its bipolar connector assembly.

FIG. 5 is sectional view through the bipolar connector assembly 24 of the lead illustrated in FIG. 1. In this view, the proximal end of connector pin 36 is visible in cross-section, and connector ring 34 is visible in cross-section. Connector pin 36 is coupled to coiled conductor 210 by means of a swaging core 200, which compresses conductor coil 210 between the interior lumen of connector pin 36 and the outer surface of swaging core 200, in a conventional fashion. An insulative sleeve 206 surrounds conductor 210, and extends distally, back through the connector assembly into molded sealing ring sleeve 212. The portion of sheath 206 between connector pin 36 and sleeve 212 is omitted in this drawing, for the sake of simplicity.

Surrounding connector pin 36 is a molded sealing ring sleeve 202, which may be fabricated of silicone rubber, which in turn is mounted to a spacer 204 which is typically fabricated of a harder plastic, such as polyurethane. Spacer 204 is molded in situ between connector pin 36 and ring 34, and is maintained in mechanical interconnection with ring 34 by means of internal threading 208, as described in U.S. Pat. No. 4,572,605, issued to Hess, et al., incorporated herein by reference in its entirety. Surrounding the proximal portion of ring 34 is a second molded sealing ring sleeve 212, which may similarly be fabricated of silicone rubber. This much of the connector assembly 22 is conventional, and corresponds to connector assembly on currently available Medtronic pacing and defibrillation leads.

Threaded core 214 can be seen inserted into the lumen at the distal end 216 of connector ring 34, compressing stranded conductor 108 therebetween. Core 214 and connector ring 34 may be fabricated of an implantable grade stainless steel. As described above in conjunction with threaded core 102, threaded core 214 is provided with external threading, which may be, for example, at a pitch of 125 threads per inch, a depth of 0.002", each thread having a 0.002" flat on the crest of each thread. The inner diameter of the ring electrode at its proximal end may be 0.084", with the outer diameter of the threaded portion of threaded core 214 being 0.079" and the inner diameter of the central lumen through the core being 0.063". These dimensions, in conjunction with the conductor described above provide for reliable mechanical and electrical coupling. In the specific case illustrated, the thickness of the core is chosen to allow for a slight, elastic deformation of the core as it is inserted in the lumen of the connector ring. To assemble conductor 108 to connector ring 34, it is placed along the side of threaded core 214, after which threaded core 214 is driven into the lumen at the distal end of ring electrode 34, drawing conductor 108 along, compressing it between the core 214 and the connector 34 and simultaneously shearing off the insulation on the outer surface of conductor 108, so that it makes good electrical contact with connector ring 34. As illustrated, connector ring 34 is an elongated tubular structure provided with multiple cross bores 220. Prior to installation of sealing ring sleeve 212, these cross bores are backfilled with silicone medical adhesive, allowing for interconnection of the internal components of the connector assembly with one another and with sealing ring sleeve 212, as described in the above-cited patent issued to Hess.

Figure 7:
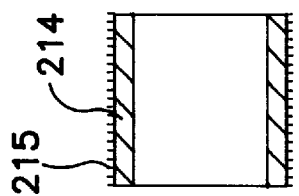
FIG. 7 is a sectional view of the threaded core illustrated in FIG. 5.
Figure 6:
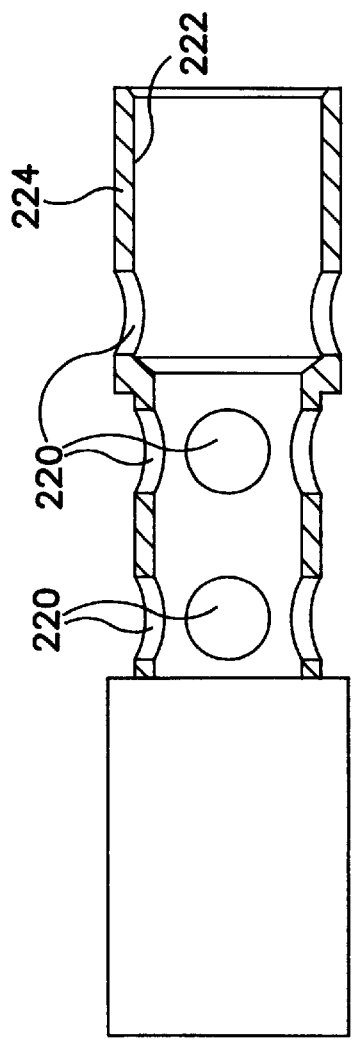
FIG. 6 is a cut-away view of the connector ring illustrated in FIG. 5.

FIG. 6 illustrates a cutaway view through connector ring 34, showing the configuration of the lumen 222 at its proximal end in more detail, and also illustrating the cross bores 220 in more detail. In this view it can be seen that the central portion of connector ring 34 is provided with two sets of intersecting cross bores, while the proximal portion is provided with a single cross bore. FIG. 7 illustrates threaded core 214, removed from the assembly illustrated in FIG. 5.

In the above description, specific dimensions, conductor types and so forth are given which the inventors have found to provide workable interconnections in conjunction with the specific embodiments disclosed above. However, it is believed that the method of interconnection provided by the present invention is widely applicable to the various types of stranded conductors proposed for use in implantable medical leads. It must understood that the relative dimensions of the internal lumen of the component to which the conductor is going to be connected, the outer dimensions and thread dimensions of the threaded core, and the dimensions of the stranded conductor will be different for each implementation and will have to be determined empirically. Similarly, while specific thread dimensions are given above, other thread dimensions or other forms of surface texturing may be employed in the context of the present invention. For example, circumferential grooves or other texturing which provides raised edges transverse to the central axis of the core or component lumen, with depressions or grooves of sufficient depth to allow flow of insulation therein may be substituted for threading. Further, while in the specific embodiments described above the texturing is on the exterior surface of the core, it may instead or in addition be provided on the interior surface of the lumen of the component to which the conductor is to be attached. However, it is believed that, given the teaching of the present application, this can readily be accomplished without undue experimentation. Finally, while the above disclosed embodiments deal specifically with interconnection of a stranded conductor to an electrode and to a connector ring on a connector assembly, the basic connection technique is equally applicable to interconnection of a stranded wire to a physiologic sensor or other component of an implantable medical lead. As such, the above disclosure should be considered exemplary, rather than limiting, with regard to the claims which follow:

We claim:

1. A method of connecting a core having a central axis and an external surface to a stranded conductor and to a component of a medical electrical lead, said component having a central axis and provided with an internal lumen having an internal surface, wherein one of said core and said component is provided with raised edges with depressions therebetween located on the inner surface of said lumen or on the outer surface of said core, said raised edges extending transverse to the central axis of said one of said core and said component having said raised edges, said core sized relative to said internal lumen such that said stranded conductor must be compressed in order to be located alongside and extending across said raised edges when said core is located in said internal lumen, comprising:

arranging said stranded conductor extending across said raised edges; and advancing said core and said stranded conductor into said lumen of said component such that said threaded surface engages said stranded conductor and retains said stranded conductor alongside said threaded surface as said core is advanced into said lumen and thereby compressing the conductor between said core and said component.

2. A method of connecting a core having a central axis and an external surface to a cable comprising a plurality of strands which in turn each comprise a number of wires and to a component of a medical electrical lead, said component having a central axis and provided with an internal lumen having an internal surface, wherein one of said core and said component is provided with raised edges with depressions therebetween, located on the inner surface of said lumen or on the outer surface of said core, said raised edges extending transverse to the central axis of said one of said core and said component having said raised edges, said core sized relative to said internal lumen such that said cable must be compressed in order to be located alongside and extending across said raised edges when said core is located in said lumen, comprising:

arranging said cable extending across said raised edges; and advancing said core and said cable into said lumen of said component such that said threaded surface engages said cable and retains said cable alongside said threaded surface as said core is advanced into said lumen, and thereby compressing said cable between said core and said component.

3. A method of connecting a core having a central axis and an external surface to a stranded conductor and to a component of a medical electrical lead, said component having a central axis and provided with an internal lumen having an internal surface, said core provided with raised edges with depressions therebetween located on the outer surface of said core, said raised edges extending transverse to the central axis of said core, said core sized relative to said internal lumen such that said stranded conductor must be compressed in order to be located alongside and extending across said raised edges when said core is located in said internal lumen, comprising:

arranging said stranded conductor extending across said raised edges; and advancing said core and said stranded conductor into said lumen of said component such that said threaded surface engages said stranded conductor and retains said stranded conductor alongside said threaded surface as said core is advanced into said lumen and thereby compressing the conductor between the raised edges and the interior surface of the interior lumen of said component.

4. A method according to claim 1, wherein said stranded conductor is provided with an insulative coating and wherein said advancing step comprises advancing said core into said lumen of said component and thereby shearing the insulative coating of said conductor away from said conductor.

5. A method according to claim 2, wherein said cable is provided with an insulative coating and wherein said advancing step comprises advancing said core into said lumen of said component and thereby shearing the insulative coating of said cable away from said conductor.

6. A method according to claim 3, wherein said conductor is provided with an insulative coating and wherein said advancing step comprises advancing said core into said lumen of said component and thereby shearing the insulative coating of said conductor away from said conductor.

7. A method according to claim 1 or claim 2 or claim 3, wherein said component is an electrode and wherein said step of advancing said core into said component comprises advancing said core into said lumen of said electrode.

8. A method according to claim 1 or claim 2 or claim 3, wherein said component is an electrical connector and wherein said step of advancing said core into said component comprises advancing said core into said lumen of said electrical connector.

9. A method according to claim 1 or claim 2 or claim 3, wherein said step of advancing said core into said component comprises advancing said core into said lumen and thereby elastically deforming said core.

* * * * *